(12) United States Patent
Yoshikawa

(10) Patent No.: US 7,985,872 B2
(45) Date of Patent: Jul. 26, 2011

(54) METHOD FOR PRODUCING OLEFIN COMPOUND

(75) Inventor: Kouji Yoshikawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 625 days.

(21) Appl. No.: 12/096,026

(22) PCT Filed: Dec. 12, 2006

(86) PCT No.: PCT/JP2006/025143
§ 371 (c)(1),
(2), (4) Date: Jun. 24, 2008

(87) PCT Pub. No.: WO2007/069761
PCT Pub. Date: Jun. 21, 2007

(65) Prior Publication Data
US 2009/0036620 A1 Feb. 5, 2009

(30) Foreign Application Priority Data
Dec. 13, 2005 (JP) .................. 2005-358632

(51) Int. Cl.
*C07C 67/317* (2006.01)
*C07D 317/50* (2006.01)

(52) U.S. Cl. ....................... 560/124; 549/434

(58) Field of Classification Search .......... None
See application file for complete search history.

(56) References Cited

U.S. PATENT DOCUMENTS
7,700,799 B2 * 4/2010 Yoshikawa .................. 560/124

FOREIGN PATENT DOCUMENTS
EP 1 728 781 A1 12/2006
JP 41-1532 B1 2/1966
WO 2005/090280 A1 9/2005

OTHER PUBLICATIONS

N. Hoffman et al., "Palladium-Catalyzed Decarbonylation of trans-alpha-Substituted Cinnamaldehydes", J. Org. Chem., 27, (1962), pp. 2687-2689.
Bensadat, Abdelkader et al., Synthesis of diethyl3- (trifluoromethyl) glutamate, Bulletin de la Societe Chimiquede France, (1996), 133 (5), pp. 509-514.
Laurent, A. et al., Synthesis of trifluoromethyl alkenes andalkynes. Trifluoromethyl captodative olefins, TetrahedronLetters, (1991), 32 (26), pp. 3071-3074.

* cited by examiner

*Primary Examiner* — Brian J Davis
(74) *Attorney, Agent, or Firm* — Sughrue Mion, PLLC

(57) ABSTRACT

A method for producing an olefin compound represented by the formula (2):

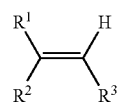

(2)

wherein $R^1$ and $R^2$ are the same or different, and independently represent an alkyl group or the like, with the proviso that $R^1$ and $R^2$ are not hydrogen atoms at the same time, $R^3$ represents an alkyl group or the like, which comprises contacting a palladium catalyst with an α,β-unsaturated aldehyde compound represented by the formula (1):

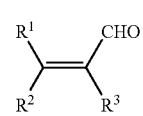

(1)

wherein $R^1$, $R^2$ and $R^3$ are the same as defined above, in the presence of an inorganic base.

7 Claims, No Drawings

METHOD FOR PRODUCING OLEFIN COMPOUND

TECHNICAL FIELD

The present invention relates to a method for producing an olefin compound.

BACKGROUND ART

Olefin compounds are important compounds as pharmaceuticals, agrichemicals and intermediates thereof. For example, 2,2-dimethyl-3-[(1Z)-1-propenyl]cyclopropanecarboxylic acid ester has been known as a synthetic intermediate of pyrethroid type household agents for epidemic prevention and insecticides.

As a method for producing the olefin compound, J. Org. Chem., 27, 2687 (1962) and WO 2005/090280 disclose a method comprising contacting an α,β-unsaturated aldehyde compound with a palladium catalyst.

DISCLOSURE OF THE INVENTION

The present invention provides a method for producing an olefin compound represented by the formula (2):

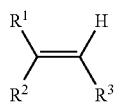

(2)

wherein $R^1$ and $R^2$ are the same or different, and independently represent a hydrogen atom;
an alkyl group which may be substituted with at least one selected from a group consisting of a halogen atom, a C1-C3 alkoxy group, a C6-C12 aryloxy group and a C2-C4 alkoxycarbonyl group;
an alkenyl group which may be substituted with at least one selected from a group consisting of a halogen atom, a C1-C3 alkoxy group, a C6-C12 aryloxy group and a C2-C4 alkoxycarbonyl group;
an aryl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group;
a heteroaryl group which may be substituted with at least one selected from a group consisting of a halogen atom, a C1-C3 alkoxy group, a C6-C12 aryloxy group and a C2-C4 alkoxycarbonyl group;
an aralkyl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group; or
a heteroaralkyl group which may be substituted with at least one selected from a group consisting of a halogen atom, a C1-C3 alkoxy group, a C6-C12 aryloxy group and a C2-C4 alkoxycarbonyl group, with the proviso that $R^1$ and $R^2$ are not hydrogen atoms at the same time,
$R^3$ represents an alkyl group which may be substituted with at least one selected from a group consisting of a halogen atom, a C1-C3 alkoxy group, a C6-C12 aryloxy group and a C2-C4 alkoxycarbonyl group;
an alkenyl group which may be substituted with at least one selected from a group consisting of a halogen atom, a C1-C3 alkoxy group, a C6-C12 aryl group, a C6-C12 aryloxy group and a C2-C4 alkoxycarbonyl group;
an aryl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group;
a heteroaryl group which may be substituted with at least one selected from a group consisting of a halogen atom, a C1-C3 alkoxy group, a C6-C12 aryloxy group and a C2-C4 alkoxycarbonyl group;
an aralkyl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group; or
a heteroaralkyl group which may be substituted with at least one selected from a group consisting of a halogen atom, a C1-C3 alkoxy group, a C6-C12 aryloxy group and a C2-C4 alkoxycarbonyl group, or
$R^1$ and $R^2$, or $R^2$ and $R^3$ may be bonded to form a ring together with carbon atoms to which they are bonded, which comprises contacting a palladium catalyst with an α,β-unsaturated aldehyde compound represented by the formula (1):

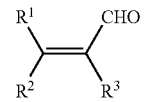

(1)

wherein $R^1$, $R^2$ and $R^3$ are the same as defined above, in the presence of an inorganic base.

BEST MODE FOR CARRYING OUT THE PRESENT INVENTION

In the α,β-unsaturated aldehyde compound represented by the formula (1) (hereinafter, simply referred to as the unsaturated aldehyde (1)), $R^1$ and $R^2$ are the same or different, and independently represent a hydrogen atom; an alkyl group which may be substituted with at least one selected from a group consisting of a halogen atom, a C1-C3 alkoxy group, a C6-C12 aryloxy group and a C2-C4 alkoxycarbonyl group;
an alkenyl group which may be substituted with at least one selected from a group consisting of a halogen atom, a C1-C3 alkoxy group, a C6-C12 aryloxy group and a C2-C4 alkoxycarbonyl group;
an aryl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group;
a heteroaryl group which may be substituted with at least one selected from a group consisting of a halogen atom, a C1-C3 alkoxy group, a C6-C12 aryloxy group and a C2-C4 alkoxycarbonyl group;
an aralkyl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group; or
a heteroaralkyl group which may be substituted with at least one selected from a group consisting of a halogen atom, a C1-C3 alkoxy group, a C6-C12 aryloxy group and a C2-C4 alkoxycarbonyl group.

Examples of the halogen atom include a fluorine atom. Examples of the C1-C3 alkoxy group include a methoxy group, an ethoxy group, an n-propoxy group and an isopropoxy group. Examples of the C6-C12 aryl group include a phenyl group and a naphthyl group. Examples of the C6-C12 aryloxy group include a phenoxy group and a naphthoxy group. Examples of the C2-C4 alkoxycarbonyl group include a methoxycarbonyl group, an ethoxycarbonyl group, an n-propoxycarbonyl group and an isopropoxycarbonyl group. Examples of the C1-C3 alkylenedioxy group include a methylenedioxy group, an ethylenedioxy group and a propylenedioxy group.

Examples of the alkyl group of the alkyl group which may be substituted with at least one selected from a group consisting of a halogen atom, a C1-C3 alkoxy group, a C6-C12 aryloxy group and a C2-C4 alkoxycarbonyl group include a straight chain, branched chain or cyclic C1-C20 alkyl group such as a methyl group, an ethyl group, an n-propyl group, an isopropyl group, an n-butyl group, an isobutyl group, a sec-butyl group, a tert-butyl group, an n-pentyl group, an n-hexyl group, a cyclopropyl group, a 2,2-dimethylcyclopropyl group, a cyclopentyl group, a cyclohexyl group, a menthyl group and a 3,7-dimethyl-2,4,5,6,7,7a-hexahydro-1H-inden-4-yl group.

Examples of the alkyl group substituted with at least one selected from a group consisting of a halogen atom, a C1-C3 alkoxy group, a C6-C12 aryloxy group and a C2-C4 alkoxycarbonyl group include a trifluoromethyl group, a pentafluoroethyl group, a methoxymethyl group, a 2-ethoxyethyl group, a 2-methoxycarbonylethyl group, a 3-ethoxycarbonylpropyl group, a 3-methoxycarbonyl-2,2-dimethylcyclopropyl group, a 3-ethoxycarbonyl-2,2-dimethylcyclopropyl group and a 3-n-propoxycarbonyl-2,2-dimethylcyclopropyl group.

Examples of the alkenyl group of the alkenyl group which may be substituted with at least one selected from a group consisting of a halogen atom, a C1-C3 alkoxy group, a C6-C12 aryloxy group and a C2-C4 alkoxycarbonyl group include a straight chain, branched chain or cyclic C1-C10 alkenyl group such as an ethenyl group, a 2-propenyl group, a 2-butenyl group, a 3-butenyl group, a 2-methyl-2-propenyl group, a 2-cyclohexenyl group, a 1-ethyl-3-butenyl group, a 3-methyl-3-butenyl group, a 4-methyl-4-pentenyl group and a 1-hexen-4-yl group.

Examples of the alkenyl group substituted with at least one selected from a group consisting of a halogen atom, a C1-C3 alkoxy group, a C6-C12 aryloxy group and a C2-C4 alkoxycarbonyl group include a 3-fluoro-2-propenyl group, a 3,3-difluoro-2-propenyl group, a 4-methoxy-2-butenyl group, a 4-phenoxy-2-butenyl group and 3-phenyl-2-propenyl group.

Examples of the aryl group of the aryl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group include a C6-C12 aryl group such as a phenyl group, a naphthyl group and a 2-methylphenyl group.

Examples of the aryl group substituted with at least one selected from a group consisting of a halogen atom, a C1-C3 alkoxy group, a C1-C3 alkylenedioxy group, a C6-C12 aryloxy group and a C2-C4 alkoxycarbonyl group include a 4-methoxyphenyl group, a 4-methoxycarbonylphenyl group, a 4-fluorophenyl group, a 4-methoxyphenyl group, a 4-phenoxyphenyl group and a 1,3-benzodioxol-5-yl group.

Examples of the heteroaryl group of the heteroaryl group which may be substituted with at least one selected from a group consisting of a halogen atom, a C1-C3 alkoxy group, a C6-C12 aryloxy group and a C2-C4 alkoxycarbonyl group include a C4-C12 heteroaryl group containing at least one heteroatom such as a 2-furyl group, a 1,3-oxazol-4-yl group and a 2-methyl-1,3-oxazol-4-yl group.

Examples of the heteroaryl group substituted with at least one selected from a group consisting of a halogen atom, a C1-C3 alkoxy group, a C6-C12 aryloxy group and a C2-C4 alkoxycarbonyl group include a 3-fluoro-2-furyl group and a 3-methoxy-2-furyl group.

Examples of the aralkyl group of the aralkyl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group include a C7-C20 aralkyl group such as a benzyl group, a 2-phenylethyl group, a 3-phenylpropyl group, a methylbenzyl group and a 4-phenylcyclohexyl group.

Examples of the aralkyl substituted with at least one selected from a group consisting of a halogen atom, a C1-C3 alkoxy group, a C1-C3 alkylenedioxy group, a C6-C12 aryloxy group and a C2-C4 alkoxycarbonyl group include a fluorobenzyl group, a methoxybenzyl group, a phenoxybenzyl group and a 1-methyl-2-(1,3-benzodioxol-5-yl)ethyl group.

Examples of the heteroaralkyl group of the heteroaralkyl group which may be substituted with at least one selected from a group consisting of a halogen atom, a C1-C3 alkoxy group, a C6-C12 aryloxy group and a C2-C4 alkoxycarbonyl group include a C5-C12 heteroaralkyl group such as a furfuryl group.

Examples of the heteroaralkyl group substituted with at least one selected from a group consisting of a halogen atom, a C1-C3 alkoxy group, a C6-C12 aryloxy group and a C2-C4 alkoxycarbonyl group include a 3-fluoro-2-furfuryl group and a 3-methoxy-2-furfuryl group.

$R^1$ and $R^2$ may be bonded to form a ring together with carbon atoms to which they are bonded, and examples of the ring include a cycloalkylidene ring such as a cyclopentylidene ring, a cyclohexylidene ring, a 2,2-dimethylcyclohexylidene ring and a 3-isopropenylcyclohexylidene ring.

$R^2$ and $R^3$ may be bonded to form a ring together with carbon atoms to which they are bonded, and examples of the ring include a cycloalkene ring such as a cyclobutene ring, a cyclopentene ring, a cyclohexene ring, a cycloheptene ring, a cyclooctene ring, a 3,3-dimethyl-cyclohexene ring, a 4-isopropenylcyclohexene ring and a 3,5-methylene-4,4-dimethylcyclohexene ring, and a bicycloalkene ring such as a 6,6-dimethylbicyclo[3.1.1]-2-heptene ring.

The unsaturated aldehyde wherein $R^1$ is a hydrogen atom is preferably used in viewpoint that a Z-olefin compound, which is difficult to produce selectively by other producing methods, can be obtained.

In viewpoint that useful olefin compounds as synthetic intermediates of pyrethroid type household agents for epidemic prevention and insecticides are obtained, the unsaturated aldehyde wherein $R^1$ or $R^2$ is a group represented by the following formula:

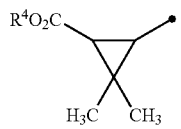

wherein $R^4$ represents a hydrogen atom; an alkyl group which may be substituted with at least one selected from a group consisting of a halogen atom, a C1-C3 alkoxy group, a C6-C12 aryloxy group and a C2-C4 alkoxycarbonyl group; an alkenyl group which may be substituted with at least one selected from a group consisting of a halogen atom, a C1-C3 alkoxy group, a C6-C12 aryl group, a C6-C12 aryloxy group and a C2-C4 alkoxycarbonyl group;

an aryl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group; or an aralkyl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group; and * represents a bonding site to the carbon atom, is preferably used.

Examples of the unsaturated aldehyde (1) include 2,6,6-trimethylcyclohexene-1-carbaldehyde, (2E)-2-ethyl-2-hexenal, (2E)-2-isopropyl-5-methyl-2-hexenal, 1-cyclohexene-1-carbaldehyde, 6,6-dimethylbicyclo[3.1.1]-2-heptene-2-carbaldehyde, (2E)-2,4-diethylhepta-2,6-dienal, 4-isopropenyl-1-cyclohexene-1-carbaldehyde, (2E)-3-(3,7-dimethyl-2,4,5,6,7,7a-hexahydro-1H-inden-4-yl)-2-methyl-2-propenal, (2E)-2-methyl-3-phenyl-2-propenal, (2E)-2-hexyl-3-phenyl-2-propenal, (2E)-2-phenyl-2-butenal, (2E)-4-methyl-2-phenyl-2-pentenal, (2E)-2-(2-furyl)-2-methyl-2-propenal, (2E)-2-methyl-3-(2-methyl-1,3-oxazol-4-yl)-2-propenal, (2E)-5-(1,3-benzodioxol-5-yl)-2,4-dimethyl-2-pentenal, methyl 2,2-dimethyl-3-[(1E)-2-formyl-1-propenyl]cyclopropanecarboxylate, ethyl 2,2-dimethyl-3-[(1E)-2-formyl-1-propenyl]cyclopropanecarboxylate, n-propyl 2,2-dimethyl-3-[(1E)-2-formyl-1-propenyl]cyclopropanecarboxylate, methyl 2,2-dimethyl-3-[(1E)-2-formyl-1-hexenyl]cyclopropanecarboxylate, methyl 2,2-dimethyl-3-[(1E)-2-formyl-3,3,3-trifluoro-1-propenyl]cyclopropanecarboxylate, methyl 2,2-dimethyl-3-[(1E)-2-formyl-1,3-hexadienyl]cyclopropanecarboxylate, methyl 2,2-dimethyl-3-[(1E)-2-formyl-2-phenylethenyl]cyclopropanecarboxylate, methyl 2,2-dimethyl-3-[(1E)-2-formyl-3-phenyl-1-propenyl]cyclopropanecarboxylate, methyl 2,2-dimethyl-3-[(1Z)-2-formyl-1-propenyl]cyclopropanecarboxylate, ethyl 2,2-dimethyl-3-[(1Z)-2-formyl-1-propenyl]cyclopropanecarboxylate, n-propyl 2,2-dimethyl-3-[(1Z)-2-formyl-1-propenyl]cyclopropanecarboxylate, methyl 2,2-dimethyl-3-[(1Z)-2-formyl-1-hexenyl]cyclopropanecarboxylate, methyl 2,2-dimethyl-3-[(1Z)-2-formyl-3,3,3-trifluoro-1-propenyl]cyclopropanecarboxylate, methyl 2,2-dimethyl-3-[(1Z)-2-formyl-1,3-hexadienyl]cyclopropanecarboxylate, methyl 2,2-dimethyl-3-[(1Z)-2-formyl-2-phenylethenyl]cyclopropanecarboxylate and methyl 2,2-dimethyl-3-[(1Z)-2-formyl-3-phenyl-1-propenyl]cyclopropanecarboxylate.

A commercially available unsaturated aldehyde (1) may be used and one produced by known methods such as a method using an aldol reaction (e.g. WO2005/090280) and a method using selenium dioxide (e.g. J. Chem. Soc. (C), 1076 (1970)) may be used.

Examples of the palladium catalyst include palladium metal; a zero-valent palladium complex such as tetrakis(triphenylphoshine)palladium(0), tris(tricyclohexylphosphine)palladium(0), and bis(dibenzylideneacetone)palladium(0); a divalent palladium complex such as bis(triphenylphosphine)palladium(II) chloride, bis(tricyclohexylphosphine)palladium(II) chloride, bis(benzonitorile)palladium(II) chloride, bis(acetonitrile)palladium(II) chloride, dichloro(1,5-cyclooctadiene)palladium(II), [1,1-bis(diphenylphosphino)ferrocene]palladium(II) chloride and palladium(II) acetylacetonate; a divalent palladium salt such as palladium(II) acetate, palladium(II) trifluoroacetate, palladium(II) chloride, palladium(II) nitrate and palladium(II) iodide; and palladium supported on a solid such as palladium/carbon, palladium/silica-alumina, palladium/silica, palladium/alumina and palladium(II) acetate/silica. Among them, palladium supported on a solid is preferable, zero-valent palladium supported on a solid is more preferable and palladium/carbon is even more preferable. The content of palladium in palladium supported on a solid is not particularly limited. A commercially available palladium catalyst is usually used.

The used amount of the palladium catalyst is 0.0001 mole or more per 1 mole of the unsaturated aldehyde (1). While there is no its upper limit, if the used amount thereof is too much, it is not advantageous economically, and therefore, the used amount thereof is practically 0.0001 to 0.1 mole and more preferably 0.002 to 0.05 mole.

Examples of the inorganic base include alkali metal carbonates such as sodium carbonate, potassium carbonate and rubidium carbonate, cesium carbonate; alkali metal hydrogen carbonates such as sodium hydrogen carbonate, potassium hydrogen carbonate, rubidium hydrogen carbonate and cesium hydrogen carbonate; and alkali metal hydroxides such as sodium hydroxide, potassium hydroxide, rubidium hydroxide and cesium hydroxide. Alkali metal carbonates and alkali metal hydroxides are preferable, and alkali metal carbonates are more preferable. The inorganic base may be in the form of a solid or an aqueous solution.

The used amount of the inorganic base is usually 0.1 to 10 moles and preferably 0.5 to 3 moles per 1 mole of palladium atom contained in the palladium catalyst.

A decarbonylation reaction proceeds by contacting the palladium catalyst with the unsaturated aldehyde (1) to generate the olefin compound represented by the formula (2) (hereinafter, simply referred to as the olefin (2)).

While the contact may be conducted in the absence of a solvent, it is usually conducted in the presence of an inert solvent on the decarbonylation reaction. Examples of the inert solvent on the decarbonylation reaction include aromatic hydrocarbon solvents such as benzene, toluene, ethylbenzene, mesitylene, cymene and chlorobenzene; aliphatic saturated hydrocarbon solvents such as hexane, cyclohexane, heptane, octane, decane and hexadecane; aliphatic unsaturated hydrocarbon solvents such as hexene, heptene, octene, decene, hexadecene, cyclohexene and cyclododecene; ester solvents such as ethyl acetate and ethyl octanoate; halogenated aliphatic hydrocarbon solvents such as dichloroethane, carbon tetrachloride and octyl chloride; nitrile solvents such as acetonitrile and benzonitrile; ether solvents such as tert-butyl methyl ether, tetrahydrofuran and dihexyl ether; and ketone solvents such as methyl isobutyl ketone and 5-nonane. The solvent may be used alone and two or more thereof may be mixed to be used. While the used amount thereof is not particularly limited, it is usually 0.5 to 100 parts by weight, and preferably 1 to 10 parts by weight per 1 part of the unsaturated aldehyde (1).

The contacting temperature is usually 70 to 250° C., and preferably 100 to 180° C.

The contact of the unsaturated aldehyde (1) and the palladium catalyst is carried out by mixing the unsaturated aldehyde (1), the palladium catalyst and the inorganic base, and the mixing order is not particularly limited. When a hydrous one is used as the palladium catalyst or an aqueous solution of the inorganic base is used, it is preferred that after mixing the palladium catalyst, the inorganic base and the solvent and removing water previously by means such as azeotropic dehydration, the unsaturated aldehyde (1) is added to the resultant mixture.

While the contact of the palladium catalyst and the unsaturated aldehyde (1) is usually conducted under normal pressure, it may be conducted under pressure.

The contacting time differs depending on the contacting temperature, and it is usually 3 to 50 hours.

The progress of the decarbonylation reaction can be checked by a conventional analytical means such as gas chromatography, high performance liquid chromatography, thin layer chromatography, nuclear magnetic resonance spectrum analysis, infrared absorption spectrum analysis and the like. Alternatively, the progress of the decarbonylation reaction can also be checked by measuring the amount of carbon monoxide generated from the reaction mixture.

Alternatively, the contact of the palladium catalyst and the unsaturated aldehyde (1) in the presence of the inorganic base and a polyether compound sometimes inhibit production of geometric isomers or regioisomers as by-products more effectively.

In the present description, "the polyether compound" means a compound having two or more ether bonds within a molecule. Examples of the polyether compound include polyalkylene glycol compounds such as polyethylene glycol and polypropylene glycol; polyalkylene glycol alkyl ether compounds such as polyethylene glycol dimethyl ether; and crown ethers such as 15-crown-5 and 18-crown-6, and polyalkylene glycol compounds are preferable and polyethylene glycol is more preferable. Polyethylene glycol having an average molecular weight of 200 to 2000 is preferable. A commercially available polyether compound is usually used. The used amount of the polyether compound is usually 0.1 to 10 parts by weight per 1 part by weight of the inorganic base.

After completion of the reaction, for example, the olefin (2) can be isolated by removing an insoluble matters from the reaction mixture by filtration followed by concentration. The obtained olefin (2) may be further purified by a conventional purification means such as rectification, column chromatography and the like.

Examples of thus obtained olefin (2) include 1,3,3-trimethylcyclohexene, (3Z)-3-heptene, (3Z)-2,6-dimethyl-3-heptene, cyclohexene, 6,6-dimethylbicyclo[3.1.1]-2-heptene, (5Z)-4-ethylocta-1,5-diene, 4-isopropenylcyclohexene, 3,7-dimethyl-4-[(1Z)-1-propenyl]-2,4,5,6,7,7a-hexahydro-1H-indene, (1Z)-1-propenylbenzene, (1Z)-1-octenylbenzene, [(1Z)-4-methyl-1-pentenyl]benzene, 2-[(1Z)-1-propenyl]furan, 2-methyl-4-[(1Z)-1-propenyl]-1,3-oxazole, 5-[(3Z)-2-methyl-3-pentenyl]-1,3-benzodioxole, methyl 2,2-dimethyl-3-[(1Z)-1-propenyl]cyclopropanecarboxylate, ethyl 2,2-dimethyl-3-[(1Z)-1-propenyl]cyclopropanecarboxylate, n-propyl 2,2-dimethyl-3-[(1Z)-1-propenyl]cyclopropanecarboxylate, methyl 2,2-dimethyl-3-[(1Z)-1-hexenyl]cyclopropanecarboxylate, methyl 2,2-dimethyl-3-[(1Z)-3,3,3-trifluoro-1-propenyl]cyclopropanecarboxylate, methyl 2,2-dimethyl-3-[(1Z)-1,3-hexadienyl]cyclopropanecarboxylate, methyl 2,2-dimethyl-3-[(1Z)-2-phenylethenyl]cyclopropanecarboxylate, methyl 2,2-dimethyl-3-[(1Z)-3-phenyl-1-propenyl]cyclopropanecarboxylate, methyl 2,2-dimethyl-3-[(1E)-1-propenyl]cyclopropanecarboxylate, ethyl 2,2-dimethyl-3-[(1E)-1-propenyl]cyclopropanecarboxylate, n-propyl 2,2-dimethyl-3-[(1E)-1-propenyl]cyclopropanecarboxylate, methyl 2,2-dimethyl-3-[(1E)-1-hexenyl]cyclopropanecarboxylate, methyl 2,2-dimethyl-3-[(1E)-3,3,3-trifluoro-1-propenyl]cyclopropanecarboxylate, methyl 2,2-dimethyl-3-[(1E)-1,3-hexadienyl]cyclopropanecarboxylate, methyl 2,2-dimethyl-3-[(1E)-2-phenylethenyl]cyclopropanecarboxylate and methyl 2,2-dimethyl-3-[(1E)-3-phenyl-1-propenyl]cyclopropanecarboxylate.

EXAMPLES

The present invention will be further illustrated in detail by Examples. The present invention is not limited to these Examples. Meanwhile, purity and Z-isomer/E-isomer ratio were calculated by gas chromatography area percentage method, and content was calculated by gas chromatography internal standard method.

Alternatively, in following Examples, the trans-isomer means one having a methoxycarbonyl group at 1-position and the substituent at 3-position on the opposite side with respect to the cyclopropane ring plane and the cis-isomer means one having a methoxycarbonyl group at 1-position and the substituent at 3-position on the same side with respect to the cyclopropane ring plane.

Example 1

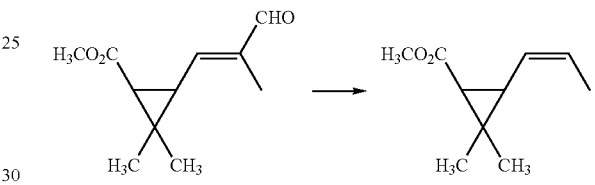

One point eight two gram of 5% by weight palladium/carbon (55% by weight hydrous), 0.077 g of potassium carbonate, 0.173 g of polyethylene glycol (average molecular weight 600), 9.6 g of mixed xylene (containing 60% by weight ethylbenzene) and 5.4 g of water were mixed and the obtained mixture was heated to 140° C. to remove water by azeotropic dehydration. To the obtained mixture, 29.9 g of a mixed xylene (containing 60% by weight ethylbenzene) solution of methyl trans-2,2-dimethyl-3-[(1E)-2-formyl-1-propenyl]cyclopropanecarboxylate (content: 50.3% by weight) was added and the resultant mixture was refluxed at 150° C. for 25 hours. After cooling the reaction mixture, palladium/carbon was removed by filtration. Palladium/carbon was washed with mixed xylene (containing 60% by weight ethylbenzene) and the obtained wash solution was mixed with the previously obtained filtrate to obtain 57.0 g of a solution containing methyl trans-2,2-dimethyl-3-(1-propenyl)cyclopropanecarboxylate. The content of methyl trans-2,2-dimethyl-3-(1-propenyl)cyclopropanecarboxylate was 20.8% by weight, the yield thereof was 92% and the Z-isomer/E-isomer ration was 99/1.

Alternatively, the conversion of methyl trans-2,2-dimethyl-3-[(1E)-2-formyl-1-propenyl]cyclopropanecarboxylate was 96% and the yield of methyl trans-2,2-dimethyl-3-(2-propenyl)cyclopropanecarboxylate was 0.48%.

Example 2

One point six five gram of 5% by weight palladium/carbon (50% by weight hydrous), 0.052 g of potassium carbonate and 15.8 g of mixed xylene (containing 7% by weight ethylbenzene) were mixed and the obtained mixture was heated to 140° C. to remove water by azeotropic dehydration. To the obtained mixture, 28.9 g of a mixed xylene (containing 7% by weight ethylbenzene) solution of methyl trans-2,2-dimethyl-3-[(1E)-2-formyl-1-propenyl]cyclopropanecarboxylate (content: 52.53% by weight) was added and the resultant mixture was refluxed at 150° C. for 43 hours. After cooling the reaction mixture, palladium/carbon was removed by filtration. Palladium/carbon was washed with mixed xylene (containing 7% by weight ethylbenzene) and the obtained wash solution was mixed with the previously obtained filtrate to obtain 77.8 g of a solution containing methyl trans-2,2-dimethyl-3-(1-propenyl)cyclopropanecarboxylate.

The content of methyl trans-2,2-dimethyl-3-(1-propenyl)cyclopropanecarboxylate was 15.6% by weight, the yield thereof was 94% and the Z-isomer/E-isomer ration was 99/1.

The conversion of methyl trans-2,2-dimethyl-3-[(1E)-2-formyl-1-propenyl]cyclopropanecarboxylate was 96% and the yield of methyl trans-2,2-dimethyl-3-(2-propenyl)cyclopropanecarboxylate was 0.58%.

Example 3

One point six five gram of 5% by weight palladium/carbon (50% by weight hydrous), 0.057 g of potassium hydroxide, 0.162 g of polyethylene glycol (average molecular weight 600) and 15.9 g of mixed xylene (containing 7% by weight ethylbenzene) were mixed and the obtained mixture was heated to 140° C. to remove water by azeotropic dehydration. To the obtained mixture, 29.4 g of a mixed xylene (containing 7% by weight ethylbenzene) solution of methyl trans-2,2-dimethyl-3-[(1E)-2-formyl-1-propenyl]cyclopropanecarboxylate (content: 51.0% by weight) was added and the resultant mixture was refluxed at 150° C. for 33 hours. After cooling the reaction mixture, palladium/carbon was removed by filtration.

Palladium/carbon was washed with mixed xylene (containing 7% by weight ethylbenzene) and the obtained wash solution was mixed with the previously obtained filtrate to obtain 75.3 g of a solution containing methyl trans-2,2-dimethyl-3-(1-propenyl)cyclopropanecarboxylate.

The content of methyl trans-2,2-dimethyl-3-(1-propenyl)cyclopropanecarboxylate was 16.6% by weight, the yield thereof was 97% and the Z-isomer/E-isomer ration was 99/1.

The conversion of methyl trans-2,2-dimethyl-3-[(1E)-2-formyl-1-propenyl]cyclopropanecarboxylate was 98% and the yield of methyl trans-2,2-dimethyl-3-(2-propenyl)cyclopropanecarboxylate was 0.47%.

Example 4

One point six five gram of 5% by weight palladium/carbon (50% by weight hydrous), 0.084 g of potassium carbonate, 0.270 g of polyethylene glycol (average molecular weight 4000) and 42.4 g of mixed xylene (containing 7% by weight ethylbenzene) were mixed and the obtained mixture was heated to 140° C. to remove water by azeotropic dehydration. To the obtained mixture, 26.7 g of a mixed xylene (containing 7% by weight ethylbenzene) solution of methyl trans-2,2-dimethyl-3-[(1E)-2-formyl-1-propenyl]cyclopropanecarboxylate (content: 86.2% by weight) was added and the resultant mixture was refluxed at 150° C. for 42 hours. After cooling the reaction mixture, palladium/carbon was removed by filtration. Palladium/carbon was washed with mixed xylene (containing 7% by weight ethylbenzene) and the obtained wash solution was mixed with the previously obtained filtrate to obtain 84.2 g of a solution containing methyl trans-2,2-dimethyl-3-(1-propenyl)cyclopropanecarboxylate.

The content of methyl trans-2,2-dimethyl-3-(1-propenyl)cyclopropanecarboxylate was 21.9% by weight, the yield thereof was 94% and the Z-isomer/E-isomer ration was 98/2.

The conversion of methyl trans-2,2-dimethyl-3-[(1E)-2-formyl-1-propenyl]cyclopropanecarboxylate was 95% and the yield of methyl trans-2,2-dimethyl-3-(2-propenyl)cyclopropanecarboxylate was 0.70%.

Comparative Example 1

Two point four zero gram of 5% by weight palladium/carbon (50% by weight hydrous) and 36.2 g of mixed xylene (containing 7% by weight ethylbenzene) were mixed and the obtained mixture was heated to 140° C. to remove water by azeotropic dehydration. To the obtained mixture, 26.8 g of a mixed xylene (containing 7% by weight ethylbenzene) solution of methyl trans-2,2-dimethyl-3-[(1E)-2-formyl-1-propenyl]cyclopropanecarboxylate (content: 85.7% by weight) and 6.2 g of a mixed xylene (containing 7% by weight ethylbenzene) were added and the resultant mixture was refluxed at 150° C. for 14 hours. After cooling the reaction mixture, palladium/carbon was removed by filtration. Palladium/carbon was washed with mixed xylene (containing 7% by weight ethylbenzene) and the obtained wash solution was mixed with the previously obtained filtrate to obtain 88.5 g of a solution containing methyl trans-2,2-dimethyl-3-(1-propenyl)cyclopropanecarboxylate. The content of methyl trans-2,2-dimethyl-3-(1-propenyl)cyclopropanecarboxylate was 21.5% by weight, the yield thereof was 96% and the Z-isomer/E-isomer ration was 97/3.

The conversion of methyl trans-2,2-dimethyl-3-[(1E)-2-formyl-1-propenyl]cyclopropanecarboxylate was 98% and the yield of methyl trans-2,2-dimethyl-3-(2-propenyl)cyclopropanecarboxylate was 2.0%.

Reference Example 1

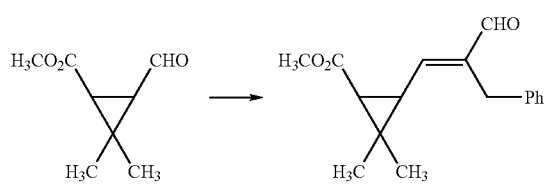

To 10.4 g of methyl 2,2-dimethyl-3-formyl-cyclopropanecarboxylate (content: 98.7% by weight), 11 g of toluene, 0.71 g of pyrrolidine and 0.62 g of acetic acid were added. To the obtained mixture, a mixed solution of 11.2 g of 3-phenyl-propanal and 21 g of toluene was added dropwise at an inner temperature of 55° C. over 6 hours. The obtained mixture was reacted at the same temperature for 1 hour. After completion of the reaction, the reaction mixture was left at rest and an aqueous layer was separated. The organic layer obtained was washed twice with 10 g of water and then once with 10 g of an aqueous solution of sodium carbonate. The organic layer obtained was concentrated under reduced pressure to obtain 21.4 g of an oily matter. The oily matter was purified by silica gel column (hexane/diethyl ether=10/2) to obtain 11.2 g of an oily matter containing methyl 2,2-dimethyl-3-[(1E)-3-phenyl-2-formyl-1-propenyl]cyclopropanecarboxylate. Meanwhile, the above-mentioned concentration was conducted with the addition of about 5 mg of 2,6-di-tert-butyl-p-cresol as a stabilizer.

Purity: 97.3%, Yield: 61%

Example 5

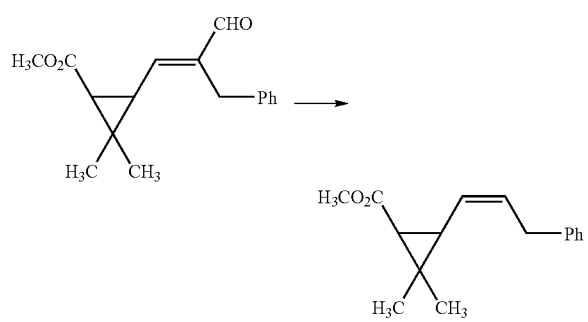

Zero point seven eight gram of 5% by weight palladium/carbon (50% by weight hydrous), 0.028 g of potassium carbonate, 0.077 g of polyethylene glycol (average molecular weight 600) and 9.2 g of mixed xylene (containing 7% by weight ethylbenzene) were mixed and the obtained mixture was heated to 140° C. to remove water by azeotropic dehydration. To the obtained mixture, 5.02 g of methyl trans-2,2-dimethyl-3-[(1E)-3-phenyl-2-formyl-1-propenyl]cyclopropanecarboxylate, which was obtained in the above-mentioned Reference Example 1, was added and the resultant mixture was refluxed at 150° C. for 17 hours. After cooling the reaction mixture, palladium/carbon was removed by filtration. The filtrate obtained was concentrated under reduced pressure to obtain 4.65 g of an oily matter. The ratio of methyl trans-2,2-dimethyl-3-[(1Z)-3-phenyl-1-propenyl]cyclopropanecarboxylate and methyl trans-2,2-dimethyl-3-[(2E)-3-phenyl-2-propenyl]cyclopropanecarboxylate in the oily matter was 97.9/2.1. The oily matter was purified by silica gel column (hexane/ethyl acetate=100/3) to obtain 3.74 g of an oily matter containing methyl trans-2,2-dimethyl-3-[(1Z)-3-phenyl-1-propenyl]cyclopropanecarboxylate.

Purity of methyl trans-2,2-dimethyl-3-[(1Z)-3-phenyl-propenyl]cyclopropanecarboxylate: 94.5%, Yield: 81% Yield of methyl trans-2,2-dimethyl-3-[(2E)-3-phenyl-2-propenyl] cyclopropanecarboxylate: 1.7%

Comparative Example 2

Zero point eight two gram of 5% by weight palladium/carbon (50% by weight hydrous) and 11 g of mixed xylene (containing 7% by weight ethylbenzene) were mixed and the obtained mixture was heated to 140° C. to remove water by azeotropic dehydration. To the obtained mixture, 5.01 g of methyl trans-2,2-dimethyl-3-[(1E)-3-phenyl-2-formyl-1-propenyl]cyclopropanecarboxylate, which was obtained in the above-mentioned Reference Example 1, was added and the resultant mixture was refluxed at 150° C. for 7 hours. After cooling the reaction mixture, palladium/carbon was removed by filtration. The filtrate obtained was concentrated under reduced pressure to obtain 4.69 g of an oily matter. The ratio of methyl trans-2,2-dimethyl-3-[(1Z)-3-phenyl-1-propenyl] cyclopropanecarboxylate and methyl trans-2,2-dimethyl-3-[(2E)-3-phenyl-2-propenyl]cyclopropanecarboxylate in the oily matter was 83.1/16.9. The oily matter was purified by silica gel column (hexane/ethyl acetate=100/3) to obtain 3.63 g of an oily matter containing methyl trans-2,2-dimethyl-3-[(1Z)-3-phenyl-1-propenyl]cyclopropanecarboxylate. Purity of methyl trans-2,2-dimethyl-3-[(1Z)-3-phenyl-propenyl]cyclopropanecarboxylate: 78.2%, Yield: 65% Yield of methyl trans-2,2-dimethyl-3-[(2E)-3-phenyl-2-propenyl]cyclopropanecarboxylate: 14%

Reference Example 2

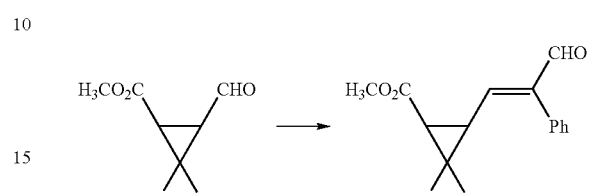

To 10.3 g of methyl 2,2-dimethyl-3-formyl-cyclopropanecarboxylate (content: 98.7% by weight), 11 g of toluene, 0.76 g of pyrrolidine and 0.69 g of acetic acid were added. To the obtained mixture, a mixed solution of 19.9 g of diethyl phthalate solution of phenylacetaldehyde (content: 50% by weight) and 20 g of toluene was added dropwise at an inner temperature of 55° C. over 6 hours. The obtained mixture was reacted at the same temperature for 1 hour. After completion of the reaction, the reaction mixture was left at rest and an aqueous layer was separated. The organic layer obtained was washed twice with 10 g of water and then once with 10 g of 10% by weight aqueous solution of sodium carbonate. The organic layer obtained was concentrated under reduced pressure to obtain 29.2 g of an oily matter. The oily matter was purified by silica gel column (hexane/diethyl ether=10/1) to obtain 17.6 g of an oily matter containing methyl 2,2-dimethyl-3-[(1E)-2-formyl-2-phenylethenyl]cyclopropanecarboxylate. Meanwhile, the above-mentioned concentration was conducted with the addition of about 5 mg of 2,6-di-tert-butyl-p-cresol as a stabilizer thereto.

The purity of methyl 2,2-dimethyl-3-[(1E)-2-formyl-2-phenylethenyl]cyclopropanecarboxylate: 94.8%, Yield: 99%

Example 6

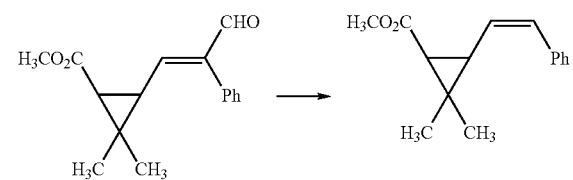

Zero point eight eight gram of 5% by weight palladium/carbon (50% by weight hydrous), 0.021 g of potassium carbonate, 4.8 g of water and 11 g of mixed xylene (containing 7% by weight ethylbenzene) were mixed and the obtained mixture was heated to 140° C. to remove water by azeotropic dehydration. To the obtained mixture, 5.13 g of methyl trans-2,2-dimethyl-3-[(1E)-2-formyl-2-phenylethenyl]cyclopropanecarboxylate, which was obtained in the above-mentioned Reference Example 2, was added and the resultant mixture was refluxed at 150° C. for 4 hours. After cooling the reaction mixture, palladium/carbon was removed by filtration. The obtained filtrate was concentrated under reduced pressure to obtain 4.68 g of an oily matter. The E-isomer/Z-isomer ratio of methyl trans-2,2-dimethyl-3-(2-phenylethenyl)cyclopropanecarboxylate in the oily matter was 94/6. The oily matter was purified by silica gel column (hexane/diethyl ether=40/1) to obtain 3.75 g of an oily matter containing methyl trans-2,2-dimethyl-3-(2-phenylethenyl)cyclopropanecarboxylate. Purity of methyl trans-2,2-dimethyl-3-(2-phenylethenyl)cyclopropanecarboxylate: 98.6%, Yield: 85%, E-isomer/Z-isomer ratio: 94/6

Comparative Example 3

Zero point nine one gram of 5% by weight palladium/carbon (50% by weight hydrous) and 11 g of mixed xylene (containing 7% by weight ethylbenzene) were mixed and the obtained mixture was heated to 140° C. to remove water by azeotropic dehydration. To the obtained mixture, 4.93 g of methyl trans-2,2-dimethyl-3-[(1E)-2-formyl-2-phenylethenyl]cyclopropanecarboxylate, which was obtained in the above-mentioned Reference Example 2, was added and the resultant mixture was refluxed at 150° C. for 3.5 hours. After cooling the reaction mixture, palladium/carbon was removed by filtration. The obtained filtrate was concentrated under reduced pressure to obtain 4.43 g of an oily matter. The E-isomer/Z-isomer ratio of methyl trans-2,2-dimethyl-3-(2-phenylethenyl)cyclopropanecarboxylate in the oily matter was 81/19. The oily matter was purified by silica gel column (hexane/diethyl ether=40/1) to obtain 3.57 g of an oily matter containing methyl trans-2,2-dimethyl-3-(2-phenylethenyl)cyclopropanecarboxylate. Purity of methyl trans-2,2-dimethyl-3-(2-phenylethenyl)cyclopropanecarboxylate: 98.4%, Yield: 84%, E-isomer/Z-isomer ratio: 81/19

Example 7

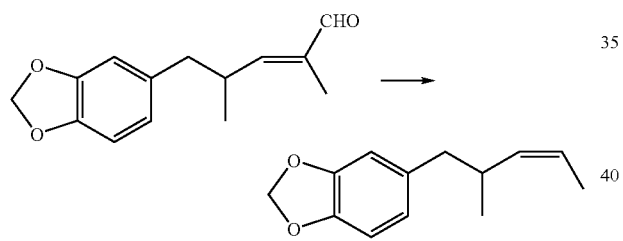

Zero point nine three gram of 5% by weight palladium/carbon (54% by weight hydrous), 0.038 g of potassium carbonate and 7 g of mixed xylene (containing 62% by weight ethylbenzene) were mixed and the obtained mixture was heated to 140° C. to remove water by azeotropic dehydration. To the obtained mixture, 4.80 g of (2E)-5-(1,3-benzodioxol-5-yl)-2,4-dimethyl-2-pentenal and 7 g of mixed xylene (containing 62% by weight ethylbenzene) were added and the resultant mixture was refluxed at 146° C. for 17 hours. After cooling the reaction mixture, palladium/carbon was removed by filtration. The obtained filtrate was concentrated under reduced pressure to obtain 4.03 g of an oily matter containing 5-(2-methyl-3-pentenyl)-1,3-benzodioxole. The area percentage of 5-(2-methyl-3-pentenyl)-1,3-benzodioxole was 82.7%. The oily matter was purified by silica gel column (hexane/ethyl acetate=40/1) to obtain 3.45 g of an oily matter containing 5-(2-methyl-3-pentenyl)-1,3-benzodioxole. The purity of 5-(2-methyl-3-pentenyl)-1,3-benzodioxole was 86.9% and the yield thereof was 73.4%.

Comparative Example 4

Zero point nine three gram of 5% by weight palladium/carbon (54% by weight hydrous), 2.8 g of water and 7 g of mixed xylene (containing 62% by weight ethylbenzene) were mixed and the obtained mixture was heated to 140° C. to remove water by azeotropic dehydration. To the obtained mixture, 4.80 g of (2E)-5-(1,3-benzodioxol-5-yl)-2,4-dimethyl-2-pentenal and 7 g of mixed xylene (containing 62% by weight ethylbenzene) were added and the resultant mixture was refluxed at 146° C. for 10 hours. After cooling the reaction mixture, palladium/carbon was removed by filtration. The obtained filtrate was concentrated under reduced pressure to obtain 3.85 g of an oily matter containing 5-(2-methyl-3-pentenyl)-1,3-benzodioxole. The area percentage of 5-(2-methyl-3-pentenyl)-1,3-benzodioxole was 62.3%. The oily matter was purified by silica gel column (hexane/ethyl acetate=40/1) to obtain 3.47 g of an oily matter containing 5-(2-methyl-3-pentenyl)-1,3-benzodioxole.

The purity of 5-(2-methyl-3-pentenyl)-1,3-benzodioxole was 64.2% and the yield thereof was 54.5%.

INDUSTRIAL APPLICABILITY

According to the reaction of the present invention, an olefin compound can be produced with inhibiting production of geometric isomers or regioisomers as by-products, and therefore, it is useful as a method for producing pharmaceuticals, agrichemicals and intermediates thereof (e.g. 2,2-dimethyl-3-[(1Z)-1-propenyl]cyclopropanecarboxylic acid ester and the like).

The invention claimed is:
1. A method for producing an olefin compound represented by the formula (2):

(2)

wherein $R^1$ and $R^2$ are the same or different, and independently represent a hydrogen atom;
an alkyl group which may be substituted with at least one selected from a group consisting of a halogen atom, a C1-C3 alkoxy group, a C6-C12 aryloxy group and a C2-C4 alkoxycarbonyl group;
an alkenyl group which may be substituted with at least one selected from a group consisting of a halogen atom, a C1-C3 alkoxy group, a C6-C12 aryloxy group and a C2-C4 alkoxycarbonyl group;
an aryl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group;
a heteroaryl group which may be substituted with at least one selected from a group consisting of a halogen atom, a C1-C3 alkoxy group, a C6-C12 aryloxy group and a C2-C4 alkoxycarbonyl group;
an aralkyl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group; or
a heteroaralkyl group which may be substituted with at least one selected from a group consisting of a halogen atom, a C1-C3 alkoxy group, a C6-C12 aryloxy group and a C2-C4 alkoxycarbonyl group, with the proviso that $R^1$ and $R^2$ are not hydrogen atoms at the same time, $R^3$ represents an alkyl group which may be substituted with at least one selected from a group consisting of a halogen atom, a C1-C3 alkoxy group, a C6-C12 aryloxy group and a C2-C4 alkoxycarbonyl group;

an alkenyl group which may be substituted with at least one selected from a group consisting of a halogen atom, a C1-C3 alkoxy group, a C6-C12 aryl group, a C6-C12 aryloxy group and a C2-C4 alkoxycarbonyl group;

an aryl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group;

a heteroaryl group which may be substituted with at least one selected from a group consisting of a halogen atom, a C1-C3 alkoxy group, a C6-C12 aryloxy group and a C2-C4 alkoxycarbonyl group;

an aralkyl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group; or a heteroaralkyl group which may be substituted with at least one selected from a group consisting of a halogen atom, a C1-C3 alkoxy group, a C6-C12 aryloxy group and a C2-C4 alkoxycarbonyl group, or $R^1$ and $R^2$, or $R^2$ and $R^3$ may be bonded to form a ring together with carbon atoms to which they are bonded, which comprises contacting a palladium catalyst with an α,β-unsaturated aldehyde compound represented by the formula (1):

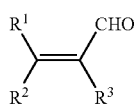

(1)

wherein $R^1$, $R^2$ and $R^3$ are the same as defined above, in the presence of an inorganic base.

2. The method according to claim 1, wherein the inorganic base is an alkali metal carbonate or an alkali metal hydroxide.

3. The method according to claim 1, wherein the palladium catalyst is palladium supported on a solid.

4. The method according to claim 3, wherein palladium supported on a solid is palladium/carbon.

5. The method according to claim 1, wherein $R^1$ is a hydrogen atom.

6. The method according to claim 1, wherein $R^1$ or $R^2$ is a group represented by the following formula:

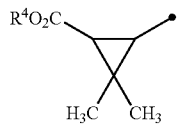

wherein $R^4$ represents a hydrogen atom; an alkyl group which may be substituted with at least one selected from a group consisting of a halogen atom, a C1-C3 alkoxy group, a C6-C12 aryloxy group and a C2-C4 alkoxycarbonyl group;

an alkenyl group which may be substituted with at least one selected from a group consisting of a halogen atom, a C1-C3 alkoxy group, a C6-C12 aryl group, a C6-C12 aryloxy group and a C2-C4 alkoxycarbonyl group;

an aryl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group; or an aralkyl group which may be substituted with at least one selected from a group consisting of a halogen atom, a C1-C3 alkoxy group, a C1-C3 alkylenedioxy group, a C6-C12 aryloxy group and a C2-C4 alkoxycarbonyl group; and ● represents a bonding site to the carbon atom.

7. The method according to claim 1, wherein a palladium catalyst is contacted with an α,β-unsaturated aldehyde compound represented by the formula (1) in the presence of an inorganic base and a polyether compound.

* * * * *